US 6,741,937 B2

(12) United States Patent
Waldman et al.

(10) Patent No.: US 6,741,937 B2
(45) Date of Patent: May 25, 2004

(54) METHODS AND SYSTEMS FOR ESTIMATING BINDING AFFINITY

(75) Inventors: Marvin Waldman, San Diego, CA (US); Cherayathumadom M. Venkatachalam, San Diego, CA (US); Paul Kirchhoff, Ann Arbor, MI (US); Xiaohui Jiang, San Diego, CA (US)

(73) Assignee: Accelrys Inc., San Diego, CA (US)

(*) Notice: Subject to any disclaimer, the term of this patent is extended or adjusted under 35 U.S.C. 154(b) by 182 days.

(21) Appl. No.: 09/851,403

(22) Filed: May 8, 2001

(65) Prior Publication Data

US 2002/0038184 A1 Mar. 28, 2002

Related U.S. Application Data

(60) Provisional application No. 60/203,124, filed on May 8, 2000.

(51) Int. Cl.[7] .............................................. G01N 31/00
(52) U.S. Cl. ........................................................ 702/23
(58) Field of Search .............................. 702/23, 22, 30, 702/19, 27

(56) References Cited

U.S. PATENT DOCUMENTS

| 6,226,603 | B1 | * | 5/2001 | Freire et al. ................... 703/11 |
| 2002/0099506 | A1 | * | 7/2002 | Floriano et al. ............... 702/19 |
| 2003/0167135 | A1 | * | 9/2003 | Ewing ........................... 702/22 |

OTHER PUBLICATIONS

Gehlhaar, D.K. et al.; Rational Drug Design; ACS Symposium series 719) 292–311 (1999).*
Bohm et al.; Structure–Based Library Design; Molecular Modelling Merges With Combinatorial Chemistry; Combinatorial Chemistry 283–286 (2000).*
Lazaridis et al; Discrimination of The Native From Misfolded Protein Models With an Energy Function Including Implicit Solvation; J. Mol. Biol. (1998) 288, 477–487.
Jones et al.; Development and Validation of a Genetic Algorithm for Flexible Docking; J. Mol. Biol. (1997) 267, 727–748.
Rarey et al.; A Fast Flexible Docking Method Using an Incremental Construction Algorithm; J. Mol. Biol. (1996) 261, 470–489.
Bissantz, et al.; Protein–Based Virtual Screening of Chemical Databases. 1. Evaluation of Different Docking/Scoring Combinations; J. Med. Chem. 2000, 43, 4759–4767.
Kim Brusniak, et al.; Comparative Molecular Field Analysis–Based Prediction of Drug Affinities at Recombinant D1A Dopamine Receptors; J. Med. Chem. 1996, 39, 850–859.

(List continued on next page.)

Primary Examiner—Michael Nghiem
(74) Attorney, Agent, or Firm—Knobbe Martens Olson & Bear LLP

(57) ABSTRACT

Methods and systems of predicting binding affinity between a ligand and a receptor. In one embodiment, the predicted binding affinity ($pKj$) is determined by at least using a formula $pKj = C0 + C1*vdW + C2*Att\_pol + C3*(Att\_pol*Att\_pol + Rep\_pol*Rep\_pol)$. vdW represents the van der Waals interaction energy between the ligand and the receptor. Att_pol represents the surface area of the ligand forming complimentary polar interactions with the receptor. Rep_pol represents the surface area of the ligand forming uncomplimentary polar interactions with the receptor. An improved process of calculating linear interpolation of grid-based vdW energy. A first non-linear function is transformed into a less non-linear second non-linear function to reduce the error in linear interpolation. A trilinear interpolation process is applied to the second non-linear function. The value obtained is reverse transformed to produce an estimated vdW energy.

19 Claims, 6 Drawing Sheets

OTHER PUBLICATIONS

Schapira, et al.; Prediction of the Binding Energy for Small Molecules, Peptides and Proteins; J. Mol. Recognit. 1999;12:177–190.

Wilcox et al.; CoMFA–Based Prediction of Agonist Affinities at Recombinant D1 VS D2 Dopamine Receptors; J. Med. Chem. 1998, 41, 4385–4399.

Rognan et al.; Predicting Binding Affinities of Protein Ligands from Three–Dimensional Modes: Application to Peptide Binding to Class I Major Histocompatibility Proteins; J. Med. Chem. 1999, 42, 4650–4658.

Wang et al.; Score: A New Empirical Method for Estimating the Binding Affinity of a Protein–Ligand Complex; J. Mol. Model 1998, 4, 379–394.

Stahl et al.; Development of Filter Functions for Protein–Ligand Docking; Journal of Molecular Graphics and Modelling 16, 121–132, 1998.

Sotriffer et al.; Automated Docking of Ligands to Antibodies: Methods and Applications; Methods 20,280–291 (2000).

Lazaridis et al.; Effective Energy Function for Proteins in Solution; Proteins, 35:133–152 (1999).

Petrey et al.; Free Energy Determinants of Tertiary Structure and the Evaluation of Protein Models; Protein Science, (2000) 9:2181–2191.

Muegge, Ingo; Effect of Ligand Volume Correction on PMF Scoring; J. of Comp. Chem. 22,4,4–18–425 (2001).

Ewing et al.; Critical Evaluation of Search Alogorithms for Automated Molecular Docking and Database Screening; J. Comput. Chem. 18:1175–1189 (1997).

Morris et al.; Automated Docking Using a Lamarckian Genetic and an Empirical Binding Free Energy Function; J. Comp. Chem. 16, 14, 1639–1662 (1998).

Gohlke, et al.; Knowledge–Based Scoring Function to Predict Protein–Ligand Interactions; J. Mol. Biol. (2000)295, 337–356.

Lazaridies et al.; Effective Energy Functions for Protein Structure Prediction; Cur. Opin. Struct Biol. 10:139–145 (2000).

Pearlman et al.; Improved Scoring of Ligand–Protein Interactions Using OWFEG Energy Grids; J. Med. Chem, 2001, 44, 502–511.

Zou et al.; Inclusion of Solvation in Ligand Binding Free Energy Calculations Using the Generalized–Born Model; J. Am. Chem. Soc., 1999, 121, 8033–8043.

DeWitte et al.; SmoG: de Novo Design Method Based on Simple, Fast, and Accurate Free Energy Estimates. 1. Methodology and Supporting Evidence; J. Am. Chem. Soc., 1996, 118, 11733–11744.

Ha et al.; Evaluation of Docking/Scoring Approaches: A Comparative Study Based on MMP3 Inhibitors; J. Computer–Aided Mole. Design, 14, 435–448, 2000.

Jager, et al.; Localization and Quantification of Hydrophobicity: The Molecular Free Energy Density (MolFESD) Concept and its Application to Sweetness Recognition; J. Computer–Aided Mole. Design, 14:631–646, 2000.

Head et al.; Validate: A New Method for the Receptor–Based Prediction of Binding Affinities of Novel Ligands; J. Am. Chem. Soc. 1996, 118, 3959–3969.

Verkhivker, et al.; Deciphering Common Failures in Molecular Docking of Ligand–Protein Complexes; J. Computer–Aided Mole. Design, 14: 731–751, 2000.

Bohm, Hans–Joachim; Prediction of Binding Constants of Protein Ligands: A Fast Method for the Prioritization of Hits Obtained from de novo Design or 3D Database Search Programs; J .Computer–Aided Mole. Design, 12: 309–323, 1998.

So et al.; A Comparative Study of Ligand–Receptor Complex Binding Affinity Prediction Methods Based on Glycogen Phosphorylase Inhibitors; J. Computer–Aided Mole. Design, 13: 243–258; 1999.

* cited by examiner

US 6,741,937 B2

METHODS AND SYSTEMS FOR ESTIMATING BINDING AFFINITY

CROSS REFERENCE TO RELATED APPLICATIONS

This application claims priority under 35 U.S.C. §119(e) to U.S. Provisional Patent Application No. 60/203,124, entitled "Linear Prediction of Binding Affinity" and filed May 8, 2000, the entire disclosure of which is hereby incorporated by reference in its entirety.

BACKGROUND OF THE INVENTION

1. Field of the Invention

This invention relates to methods and systems of estimating the likely binding affinity between molecular entities.

2. Description of the Related Art

A wide variety of techniques for determining the energetically favored interaction geometry between two interacting molecules have been developed. In addition, once this geometry has been determined, it is often useful to further predict the binding affinity, generally expressed as the $pK_i$, of the molecules in solution. This is useful, for example, in the drug discovery process, where it is highly desirable to be able to computationally evaluate the likely effectiveness of a drug candidate compound without the need for wet chemical testing of the compound.

Various methods have been devised for estimating the likely binding affinity between chemical entities such as a drug candidate molecule (e.g., a ligand) and a protein or other form of receptor. Some methods use a mathematical model of the form:

$$pK_i = \Sigma_j C_j D_j$$

wherein $C_j$ are constant coefficients, and $D_j$ are calculated ligand-protein interaction descriptors which depend on the nature of the ligand-protein interaction (e.g. 3-D binding geometry, computed binding energies, etc.) for the specific ligand-protein system for which the $pK_i$ is being predicted.

To use the above-described method, a set of descriptors are selected which are believed to be related to binding affinity. The constant coefficients may be selected by well-known regression methods using a training set of systems whose binding affinities have been determined by experiment, and whose three-dimensional structures have also already been experimentally determined or derived computationally. In these modeling techniques, even though the true relationship between the $pK_i$ of a selected system and each of the descriptors may be poorly understood and non-linear, it is hoped that a linear combination of carefully selected descriptors can be a useful and relatively accurate predictor of $pK_i$ values.

Since many descriptors are available to be included in the above formula, it is possible to "over-fit" the training data with a large number of descriptors, in order to at least artificially fit the given training data with the many descriptors. However, if the descriptors and coefficients do not adequately reflect physical reality, then descriptors and coefficients that fit one set of training data may not fit another set of training data. Moreover, using a large number of descriptors results in a complex and difficult to understand prediction model which is often not particularly useful when applied to other systems outside the set of training data. Using a large number of descriptors also requires more computational power.

It is thus difficult to determine what set of descriptors will produce a robust and accurate model. As noted briefly above, the correlation between $pK_i$ and the atomic features of interacting molecules is very complex and generally non-linear, and the descriptors used to characterize these atomic features can take an essentially infinite number of forms. In addition, the descriptors may be interelated in physical significance, and may affect $pK_i$ in different ways depending on the types of interacting molecules.

It would thus be advantageous for the drug discovery process as well as other applications to devise descriptors for use in linear formulas for the prediction of binding affinity that result in models having relatively wide applicability and good predictive accuracy.

SUMMARY OF THE INVENTION

In one embodiment, the invention comprises a method of estimating a binding affinity between first and second interacting molecular entities. The method may comprise defining at least one surface area descriptor of the interaction, the descriptor comprising an amount of non-neutral surface area of the first molecular entity that is proximate to a non-neutral portion of the second molecular entity and using the amount of non-neutral surface area of the first molecular entity in a formula for numerically estimating the binding affinity.

In another embodiment, a method of predicting binding affinity between two molecular entities comprises determining a van der Waals interaction energy between the first molecule and the second molecule (the vdW value), determining a surface area of the first molecule forming complimentary polar interactions with the second molecule (the Att_pol value), determining a surface contact area of the first molecule forming uncomplimentary polar interactions with the second molecule (the Rep_pol value), calculating a value of $pK_i$ at least using a formula $pK_i = C0 + (C1*vdW) + (C2*Att\_pol) + (C3*((Att\_pol*Att\_pol) + (Rep\_pol*Rep\_pol)))$, based on the determined values of vdW, Att_pol, and Rep_pol, with C0, C1, C2 and C3 being constant coefficients.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

In some advantageous embodiments of the invention, the descriptors for a linear prediction formula for $pK_i$ are derived from three fundamental physical characteristics of the interaction. The first is the van der Waals energy of the molecular interaction (hereinafter denoted "vdW"). The second is the surface area of one molecule that forms a close and attractive electrical interaction with the surface of the other molecule. (hereinafter denoted "Att_pol"). The third is the surface area of one molecule that forms a close and repulsive electrical interaction with the surface of the other molecule (hereinafter denoted "Rep_pol"). As is described further below, the descriptors of advantageous linear formulas for $pK_i$ may comprise vdW, Att_pol, Rep_pol, and/or arithmetic combinations of these descriptors.

Figure 1:
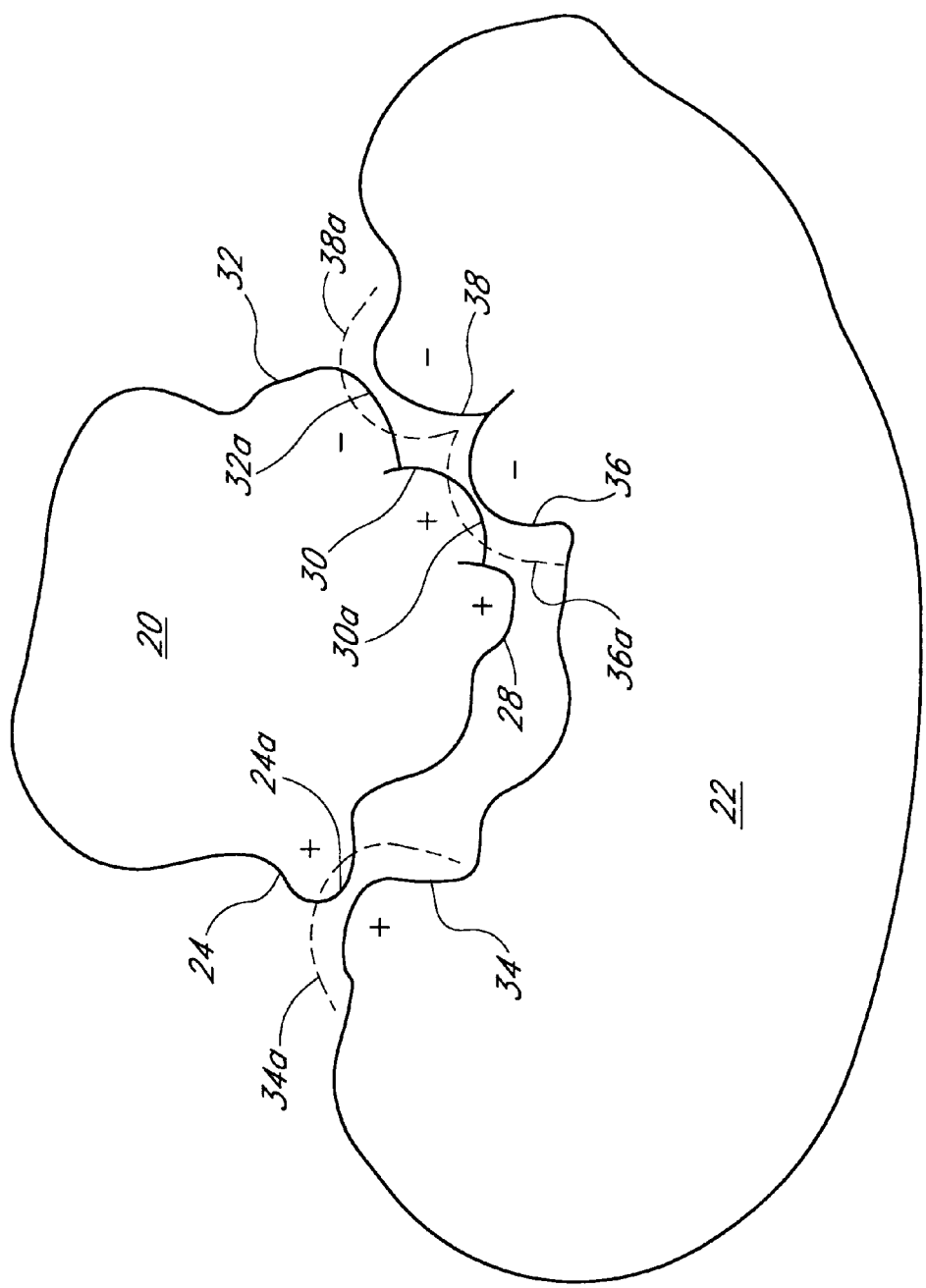
FIG. 1 is a diagram showing two interacting molecular entities.

FIG. 1 is a diagram showing an example interaction geometry of a first molecular entity 20 and a second molecular entity 22. In some cases, the first molecular entity may be a drug candidate molecule, and the second may be a protein. The first molecular entity 20 comprises atoms 24, 28, 30 and 32, with respective electrostatic charges (or partial charges) of positive, positive, positive, and negative. The second molecular entity 22 comprises atoms 34, 36, 38, with respective electrostatic charges (or partial charges) of positive, negative, and negative.

It will be appreciated that attractive and repulsive electrical interactions will occur when polar or charged atoms are in proximity to one another. Adjacent neutral atoms are thus preferably excluded from contributing to Att_pol or Rep_pol. In one embodiment, atoms with partial charges above a certain threshold (either positive or negative) are identified as polar. Atomic partial charges are commonly used as part of the computation of electrostatic interaction energies in force field calculations, and partial charge assignments for the atoms found in biological macromolecules have been created and used in a variety of contexts and are well known in the art. Some of the force field models using atomic partial charge assignments are described in U.S. Pat. No. 5,612,894 to Wertz, and in "DREIDING: A Generic Force Field for Molecular Simulations," *J. Phys. Chem.* 94, 8897–8909 (1990). An additional force field model termed "CFF", is described in *J. Comp. Chem* 15, 162–182 (1994), and in *J. Am. Chem. Soc.* 116, 2515–2525 (1994). The disclosure of U.S. Pat. No. 5,612,894 and the Journal articles described above are hereby incorporated by reference in their entireties. In one embodiment, atoms may be classified as polar or non-polar according to the type of the atoms. For example, in one implementation, oxygen, nitrogen, and halogen atoms are classified as polar and negative, and their correspondingly attached hydrogens are classified as polar and positive. In this embodiment, all other atoms are considered non-polar, and will not contribute to the calculation of Att_pol or Rep_pol. In another embodiment, a polar atom may be defined as an atom with the absolute value of Gasteiger charge of greater than about 0.15 or an absolute value of CFF partial charge of about 0.2 or more. It may be noted that in both these embodiments, atoms are only classified as having a positive polarity, negative polarity, or neutral. The degree or amount of charge or (partial charge) is not included in the calculation of Att_pol or Rep_pol.

Another requirement for incorporation of a particular charge interaction into Att_pol and Rep_pol is that the two polar atoms be close to each other. This may be quantified by defining the descriptors Att_pol and Rep_pol as the portion of the surface area of polar atoms on the first molecular entity (e.g. the ligand molecule) that fall within a scaled van der Waals volume of polar atoms on the other molecule (e.g. the protein). For example, a scaled van der Waals volume for an oxygen atom in the protein binding site may be defined as a sphere having a radius of 1.5 times the normally assigned oxygen van der Waals radius. If a portion of the normally assigned van der Waals surface of an oxygen atom on the first molecule falls within this scaled surface when the molecules are bound, that area portion is identified as one component of the sum forming Rep_pol (as both the oxygens would be classified as polar negative).

This is illustrated in FIG. 1, where the contours of the molecular entities (in solid line) are defined by the van der Waals surfaces of the atomic constituents. For the second molecular entity, scaled van der Waals surfaces (e.g. a sphere of 1.5 times the van der Waals radius) for polar atoms are shown in dotted lines. As discussed above, Att_pol may be defined as the surface area of the first molecule 20 which forms close and complimentary (i.e. positive/negative or negative/positive) polar interactions with the second molecular entity 22. In the example shown in FIG. 1, a portion 30a of the van der Waals surface of atom 30 with a positive partial charge falls within the scaled van der Waals surface 36a (with a negative partial charge) of atom 36 on the second molecular entity 22. Therefore the surface area 30a falling within the scaled surface 36a is Att_pol for the example interaction of FIG. 1.

As discussed above, Rep_pol may be defined as the surface area of the first molecule 20 which forms close and non-complimentary (i.e. negative/negative or positive/positive) polar interactions with the second molecular entity 22. In the example shown in FIG. 1, portion 24a of the van der Waals surface of atom 24 with a positive partial charge falls within the scaled van der Waals surface 34a (with a positive partial charge) of atom 34 on the second molecular entity 22. Therefore the surface area 24a falling within the scaled surface 34a is one part of Rep_pol for the example interaction of FIG. 1. The other component of Rep_pol for the example interaction of FIG. 1 is the portion 32a of atom 32 that falls within the scaled van der Waals surface 38a of atom 38. In this example, Rep_pol is the surface area 24a plus the surface area 32a.

In one advantageous embodiment, once the vdW interaction energy, Att_pol, and Rep_pol have been determined, $pK_i$ is estimated with the following formula:

$$pK_i = C0 + (C1*vdW) + (C2*Att\_pol) + (C3*((Att\_pol*Att\_pol) + (Rep\_*Rep\_pol)))$$

It can be seen that this formula includes the vdW, Att_pol, and an arithmetic combination of Att_pol and Rep_pol as descriptors.

In this formula for $pK_i$, C1 is typically a negative number, reflecting the general rule that as van der Waals energy increases, steric interference between the molecular entities is increasing, causing a decrease in binding affinity.

The term in the formula "C2*Att_pol", with typically C2>0, predicts increased binding affinity when polar groups of the two molecular entities have an electrically favorable interaction.

Another term in the formula "C3*(Att_pol*Att_pol+ Rep_pol*Rep_pol)", with typically C3<0, predicts decreased binding affinity when too many ligand polar groups are moved from water to a binding site to be placed in proximity with the protein receptor. In order to place the ligand 20 at the binding site, a desolvation penalty is typically encountered. Desolvation penalty is the energy cost in transferring a molecule from water (or another liquid) to a protein environment. Although it is desirable to move some ligand polar groups to the binding site to make favorable interaction (such as positive/negative or negative/positive interaction) with polar parts of the protein 22, the existence of the desolvation penalty makes it undesirable to move too many ligand polar groups to the binding site. As polar atoms are moved from water to the binding site, the unfavorable part "C3*(Att_pol*Att_pol+Rep_pol*Rep_pol)" is likely to dominate the favorable part "C2*Att_pol", and result in reduced binding affinity.

As described above, the coefficients C0, C1, C2 and C3 can be determined using regression methods such as least square regression fit on a training set of interacting systems. It will also be appreciated by those in the art that the coefficients produced in a regression procedure may vary depending on the details of how the numerical values for the descriptors are calculated. For example, a number of mathematical forms have been used to numerically quantify the vdW energy between atom pairs. The vdW energy between two atoms may in some embodiments be represented by a function such as $vdW = a/r^{12} - b/r^6$, with a and b being coefficients characteristics of the two interacting atoms, and r being the distance between the atomic centers. The first term, $a/r^{12}$, is usually referred to as the repulsive component of the vdW energy and the second term, $b/r^6$, as the attractive component. Alternative functional forms, such as a "soft" van der Waals potential which allows closer steric contacts have been developed and used, all of which may be used in conjuction with the present invention. Because the scoring function is intended for evaluation of experimentally determined complexes as well as docked structures derived from other calculations, there often may be errors in the docked geometries. The scoring function is advantageously somewhat tolerant of short contacts between ligand and protein atoms. Otherwise, the vdW energy descriptor will overwhelm the contribution from other descriptors. Therefore it is often desirable to "soften" the vdW function at short distances. For more details of the soft potential modification, please refer to "Protein Folding by Restrained Energy Minimization and Molecular Dynamics," M. Levitt, J. Mol. Biol., 170, 723–764 (1983), which is hereby incorporated by reference in its entirety. Grid based estimation methods which improve computation speed have also been used, and which are discussed further below. In one embodiment, the following coefficients have been derived:

$$pK_i = 0.489646 - (0.045508 * vdW\_exact\_soft) + (0.143912 * Att\_pol) - (0.00100980 * (Att\_pol^2 + Rep\_pol^2))$$

In the formula above, vdW_exact_soft represents the vdW energy computed with a softened potential function without grid-based approximation.

In another embodiment, the following coefficients and descriptors are used:

$$pK_i = 0.517527 - (0.043650 * vdW\_grid\_soft) + (0.143901 * Att\_pol) - (0.00099039 * (Att\_pol^2 + Rep\_pol^2))$$

In the formula above, vdW_grid_soft represents the soft vdW energy obtained with grid-based approximation.

It will be appreciated that in addition to vdW energy, Att_pol and Rep_pol, other descriptors can also be used in predicting binding affinity. For example, the surface area of "buried" lipophilic atom types (e.g. the amount of neutral surface area of a ligand in proximity to protein surface when bound) or the number of rotatable bonds of the ligand molecule can be used as additional descriptors. In addition, different arithmetic combinations of Att_pol and Rep_pol can be used. Several examples are as follows:

$$pK_i = C0 + C1 * vdW + C2 * Att\_pol + C3 * (Att\_pol * Att\_pol + Rep\_pol * Rep\_pol) + C4 * Rotatable\_bond.$$

$$pK_i = C0 + (C1 * Bury\_lip) + (C2 * vdW) + (C3 * Att\_pol) + (C4 * Att\_pol^2) + (C5 * Rep\_pol^2)$$

A regression analysis on a training data set produced the following coefficients in two embodiments of the above model using buried lipophilic surface, Bury_lip, as a descriptor:

$$pK_i = 1.01379 + (0.0015317 * Bury\_lip) - (0.025412 * vdW\_grid\_soft) + (0.142275 * Att\_) - (0.00075948 * Att\_pol^2) - (0.00066931 * Rep\_pol^2)$$

$$pK_i = 1.18331 + (0.00050603 * Bury\_lip) - (0.044383 * vdW\_exact\_soft) + (0.137602 * Att\_pol) - (0.00077649 * Att\_pol^2) - (0.00084378 * Rep\_pol^2).$$

Figure 2:
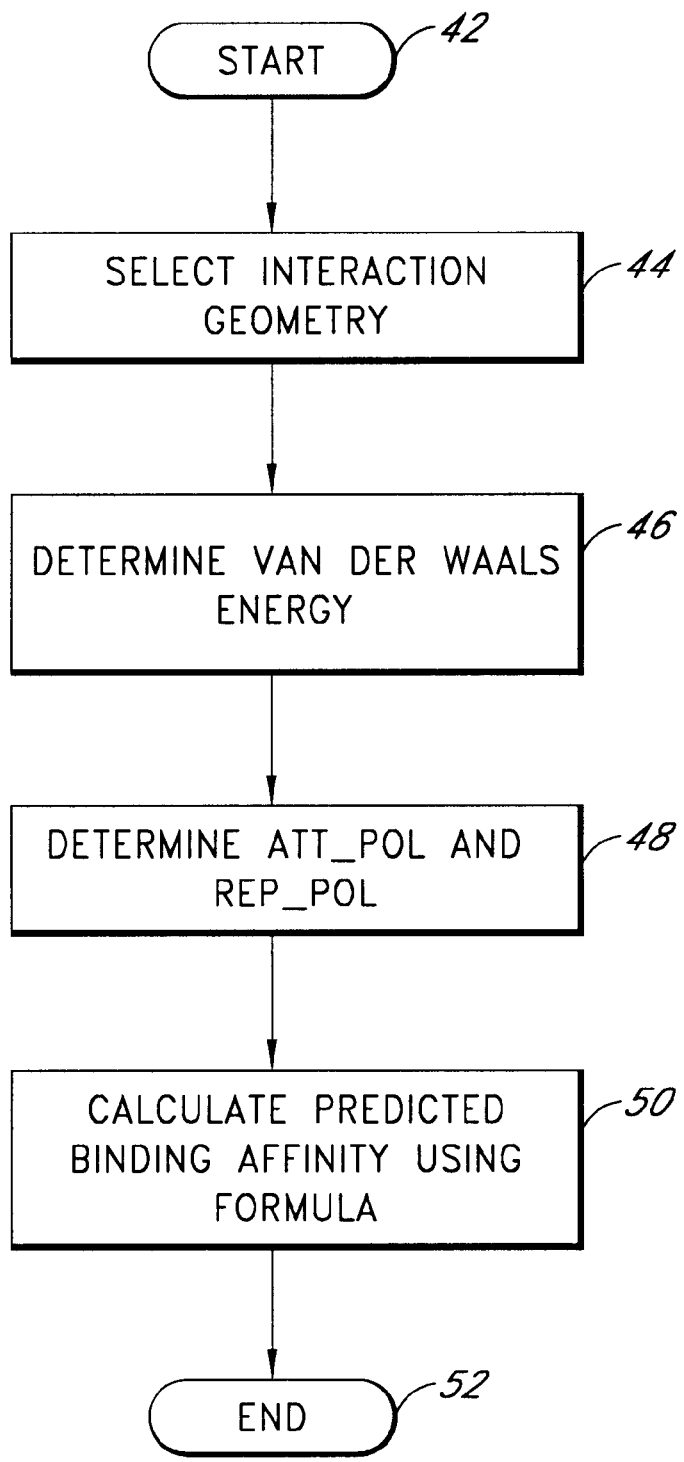
FIG. 2 is a flowchart showing one embodiment of a process of predicting binding affinity.

FIG. 2 is a flowchart showing one embodiment of a process of predicting binding affinity between two molecular entities. A start block 42 proceeds to block 44. At block 44, the process defines, retrieves, or otherwise selects an interaction geometry between two chemical entities. As described above, this may be the low energy in vacuum interaction geometry which may be determined using any of a variety of well-known techniques, both experimental and computational. At block 46, the process determines the van der Waals energy between the entities. At block 48, the process defines a portion of the surface area of one molecular entity forming complimentary (i.e. positive/negative or negative/positive) electrostatic interactions with the other molecular entity. This surface area is represented by the symbol Att_pol in the formula above. Also at block 48, the process also defines a portion of the surface area of one molecular entity forming uncomplimentary (i.e. positive/positive or negative/negative) electrostatic interactions with the protein. This surface area is represented by the symbol Rep_pol in the formula above. At block 50, the process calculates the value of $pK_i$ as the predicted binding affinity between the molecular entities using a linear combination of terms that include the computed values for the descriptors vdW energy, Att_pol, Rep_pol, and/or arithmetic combinations of these computed values. The process then proceeds to an end block 52.

The above-described process can be applied to a large number of molecular entity pairs. In a drug discovery process, those pairs with desirable predicted binding affinity values can be selected for further experimentation, thus reducing the time and effort required to identify promising pharmaceutical compounds.

Because the numerical calculation of most formulas for vdW energy between two atoms is computationally expensive, and must often be performed for thousands of atom pairs, grid based methods have been used to approximately determine vdW energies without having to perform an exact numerical calculation for all the atom pairs of the two molecular entities. In these methods, the attractive and repulsive components of the vdW potential are calculated for all the points in a three dimensional grid which is defined in the area of interest around one of the molecular entities. The vdW energies are then calculated for each of the atoms of the other molecular entity by reference to the vdW component potentials of the grid locations near each atom. In general, of course, the atoms of the bound entity do not lie exactly at grid locations, and typically some form of interpolation, often a three dimensional trilinear interpolation, between grid points surrounding the atom is used to assign a vdW energy to the atom. For a more detailed description of trilinear interpolation and its application in calculating van der Waals energies, please refer to D. Oberlin and H. A. Scheraga, "B-Spline Method for Energy Minimization in Grid-Based Molecular Mechanics Calculations" J. Comp. Chem. Vol. 19, 71–85 (1998), which is hereby incorporated by reference in its entirety. One embodiment of the trilinear interpolation method uses piecewise linear potential (PLP) scoring function to divide the range of a non-linear function into several sub-ranges, and to apply trilinear interpolation to each sub-range. For more details of the PLP scoring function, please refer to D. K. Gehlhaar, et al., Rational drug design (ACS symposium series 719) 292–311 (1999), which is hereby incorporated by reference in its entirety.

Linear interpolation introduces errors into the computed vdW values, because a linear function is being used to approximate a non-linear function. This problem is more acute for functions which include high powers of the independent variable, as is the case with distance dependence of the vdW energy. To reduce this error, one embodiment of the invention transforms the grid based vdW component potentials into a new functional form which has a lower power dependence on distance and is thus closer to linear than the actual potential function. Trilinear interpolation then is used to assign a transformed energy value to atomic positions located between grid points, and the transformed energy values are then inverse-transformed and combined into the estimated value for vdW energy. In one embodiment, each transformed energy value includes an attractive component energy value and a repulsive component energy value.

Figure 3A:
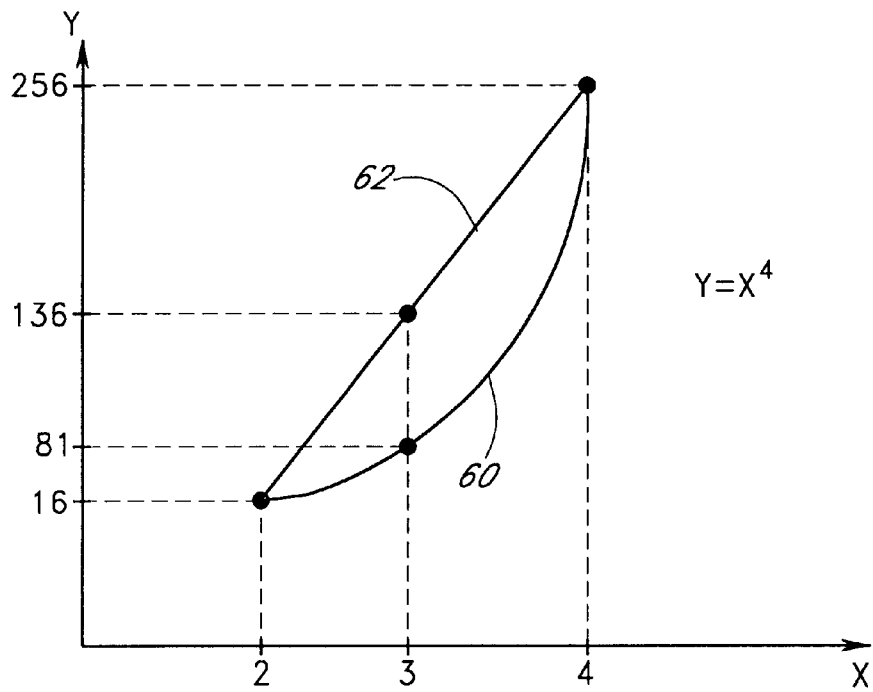
FIGS. 3A and 3B are graphs showing a method of linear interpolation used in some embodiments of the invention.
Figure 3B:
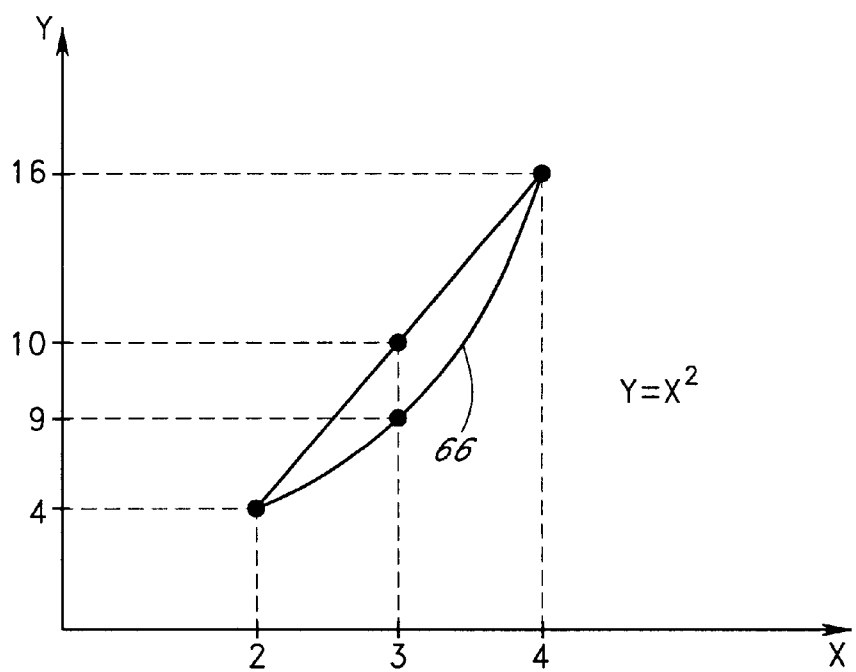

The principles of this process are illustrated by the example of FIGS. 3A and 3B. In FIG. 3A, a non-linear function $f(x)=x^4$ is shown as curve 60. The curve 60 includes endpoints (2,16) and (4,256). The curve 60 also includes a third point (3,81) which is located between the endpoints. To perform linear interpolation, a linear function is created by forming a line 62 that includes both the first point (2,16) and the second point (4,256). For x values located between 2 and 4, the linear function is then used to approximate the y values for the non-linear function. For example, and as shown in FIG. 3A, the value of y when x is equal to three would be approximated as 136.

As can be seen by this example, using a linear function to approximate a non-linear function may improve computing speed, but the approximated values include a certain error. The more "non-linear" the curve 60, the greater the error. Since vdW energy components between atom pairs are typically represented by highly non-linear terms such as $f(x)=c*x^{-6}$, $f(x)=c*x^{-9}$, and $f(x)=c*x^{-12}$, with x being the distance between the atomic centers, the errors in linear interpolation can be quite large.

To reduce this error, each of the components of the vdW function f(x) can be transformed to a new function $g(x)=[f(x)]^{1/t}$, where t is an integer which is greater than 1, but less than the characteristic power of the function f(x). Referring now to FIG. 3B as a simple example, the function $x^4$ can be transformed to the function $x^2$ by selecting t=2. The function $g(x)=x^2$ is illustrated as curve 66 in FIG. 3B, with endpoints (2,4) and (4,16). Linear interpolation can be used on this function to produce an estimated value at x=3 of 10. To transform this value into an estimation of the value of f(x) at x=3, the linear approximation of g(x) at x=3 is raised to the power t, in this case 2, producing an estimate of 100 for f(x) at x=3. The value 100 is closer to the true value of 81 for $(3)^4$ than the original linear interpolation, which produced an approximation of 136 for $x^4$ at x=3. In the case of vdW, values for a function with a lower power dependence on distance are derived in the grid based linear interpolation process. After approximate values are determined for this more linear function, the values are raised to the power necessary to transform the result into the actual functional dependence of vdW attractive and repulsive components on distance.

Figure 4:
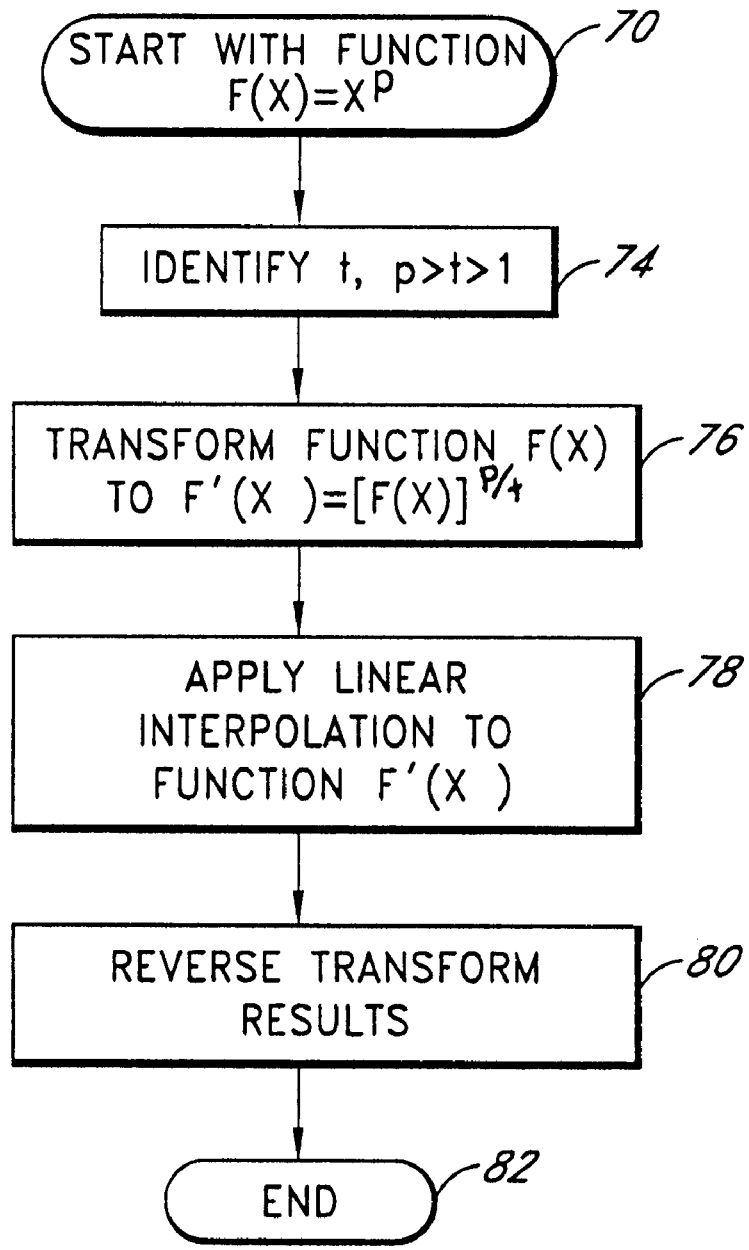
FIG. 4 is a flowchart showing one embodiment of an improved process of linear interpolation to reduce approximation error.

FIG. 4 is a flowchart showing one embodiment of this process of linear interpolation to reduce approximation error. Although two-dimensional linear interpolation is described for ease of illustration, three-dimension functions and trilinear interpolation will generally be used in the described process. The non-linear function to be approximated is represented by the function $f(X)=c*X^p$. $X_1$ and $X_2$ are boundary points with respective known values of $f(X_1)$ and $f(X_2)$, $X_3$ is a point between $X_1$ and $X_2$ whose unknown value $f(X_3)$ is to be approximated. A start block 70 proceeds to a block 74.

At block 74, a t value is selected as a positive number greater than 1 but less than the absolute value of p. For example, if p is 6 or –6, then t can be 2, 3, or another positive number greater than 1 but less than 6. The process proceeds from block 74 to block 76. At block 76, the original function $f(X)=c*X^p$ is transformed into the transformed function $f'(X)=c*X^{p/t}$. Since the absolute value of p/t is less than the absolute value of p, the transformed function f'(X) is less non-linear than the original non-linear function f(X).

The process proceeds from block 76 to block 78. At block 78, linear interpolation is applied to the transformed function $f'(X')=c*X^{p/t}$ to approximate the value of $f'(X_3)$, based on the boundary values $f'(X_1)$ and $f'(X_2)$. At block 80, a reverse transformation is applied to the approximated value $f'(X_3)$ by raising this value to the power t, to obtain the approximated value of $f(X_3)$. The process then moves to the end block 82. The process described in connection with FIG. 4 can be applied to each of the non-linear components of the function used in calculating van der Waals energy. The process can also be applied to a combined function that includes all of the non-linear components of the function.

Figure 5:
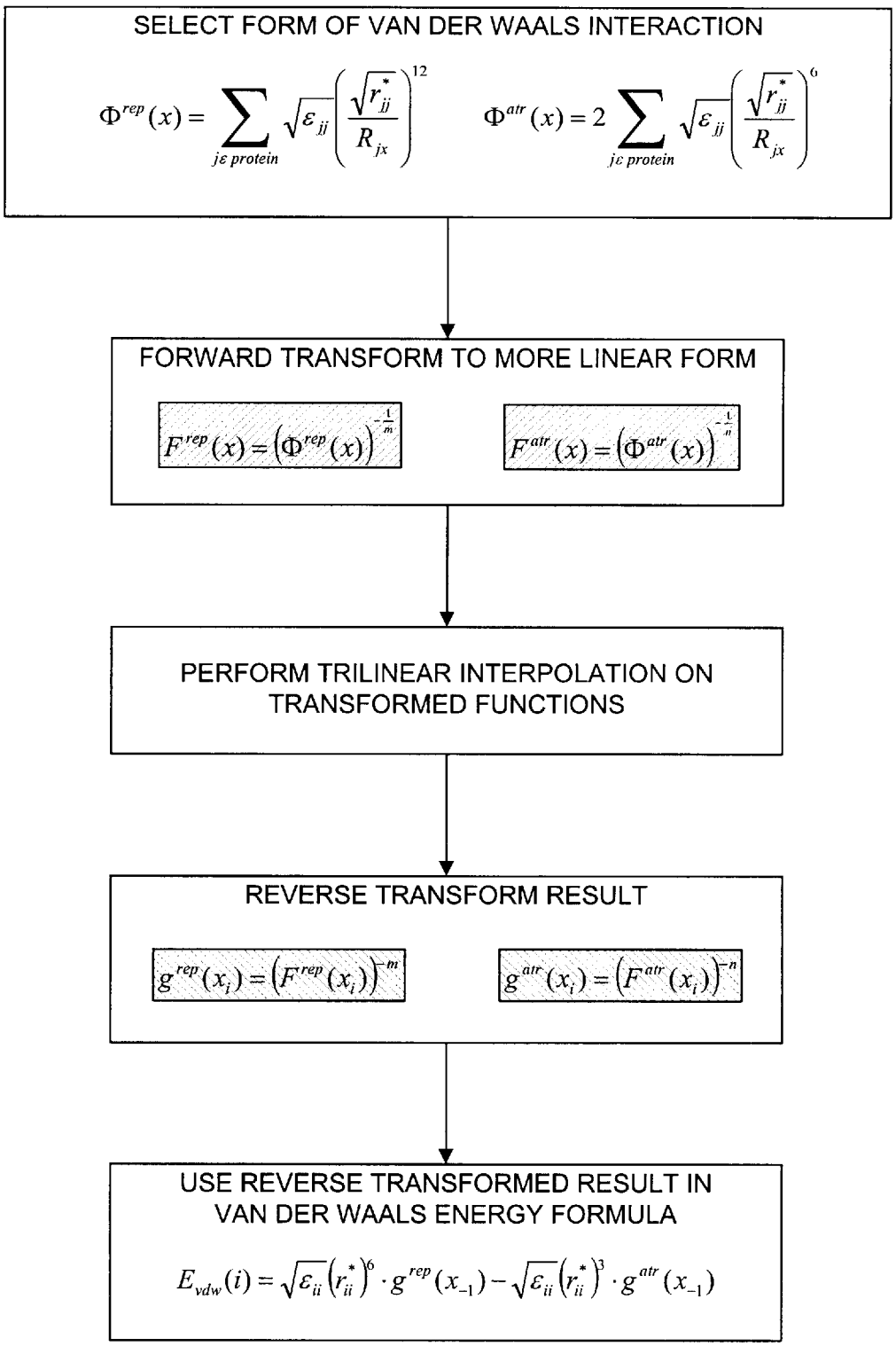
FIG. 5 is a flow chart showing one embodiment of the improved process of linear interpolation applied to a van der Walls interaction energy function.

FIG. 5 illustrates one embodiment of the method of FIG. 4 as applied to standard functional forms for the repulsive and attractive components of van der Waals interaction energy. It will be appreciated however that the interpolation method described herein is applicable to the computation of numerical values for any highly non-linear function in any context, with the computation of van der Waals interaction energy being simply one application.

Figure 6:
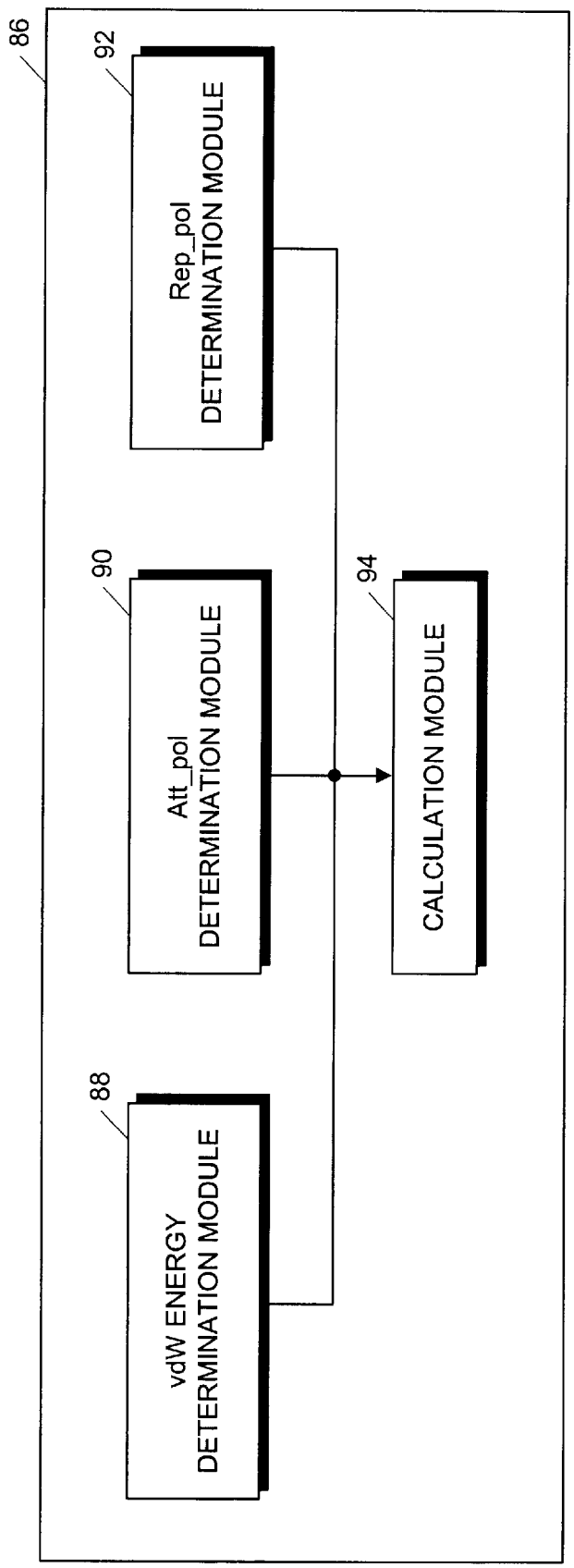
FIG. 6 is a diagram showing one embodiment of a binding affinity prediction system.

FIG. 6 is a diagram showing one embodiment of a binding affinity prediction system 86. The system 86 includes a vdW energy determination module 88, an Att_pol determination module 90, a Rep_pol determination module 92, and a calculation module 94. As those of ordinary skill in the art will appreciate, the modules of the system 86 can be combined or separated into more or fewer modules.

The vdW energy determination module 88 calculates a van der Waals energy of interaction between the molecular entities. In some embodiments, this is performed with the process of trilinear interpolation of a transformed function as described above with reference to FIGS. 3A, 3B, 4, and 5.

The Att_pol and Rep_pol determination modules 90 and 92 may advantageously calculate surface areas of electrostatic interaction with the methods described above with reference to FIG. 1. The calculation module 94 uses a linear formula including the vdW energy, Att_pol and Rep_pol values, and calculates the value of $pK_i$ as the predicted binding affinity between the molecules. Other formulas and other descriptors, such as the alternative embodiments described above can also be used by the calculation module to predict binding affinity between a molecule and a protein receptor.

In one embodiment, the system 86 also includes a coefficient determination module (not shown) that determines the coefficients of the formula used by the calculation module 94, such as the coefficients C0, C1, C2, and C3 of the formula $pK_i=C0+(C1*vdW)+(C2*Att\_pol)+(C3*(Att\_pol*Att\_pol+Rep\_pol*Rep\_pol))$. The coefficient determination module determines the coefficients by using a regression method such as least square regression fit on a training set of ligand-protein items whose binding affinities have already been determined. One embodiment of the system 86 does not include a coefficient determination module, because the coefficients have already been determined prior to using the system 86.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. As used in the Application including the claims, the word "module" refers not only to logic coded as a collection of software instructions, but also refers to logic embodied in hardware or firmware. The scope of the invention should therefore be construed in accordance with the appended claims and any equivalents thereof.

What is claimed is:

1. A method of estimating a binding affinity between first and second interacting molecular entities, said method comprising:
    defining at least one surface area descriptor of the interaction, said descriptor comprising an amount of non-neutral surface area of the first molecular entity that is proximate to a non-neutral portion of the second molecular entity, and
    using a non-linear function of said amount of non-neutral surface area of the first molecular entity as at least a component of a term in a linear formula for numerically estimating said binding affinity.

2. The method of claim 1, comprising defining an amount of surface area of the first molecular entity having a first charge polarity that is proximate to a portion of the second molecular entity having the same charge polarity.

3. The method of claim 2, comprising defining an amount of surface area of the first molecular entity having a first charge polarity that is proximate to a portion of the second molecular entity having the opposite charge polarity.

4. The method of claim 1, additionally comprising calculating a van der Waals interaction energy between said first molecular entity and said second molecular entity.

5. The method of claim 1, wherein said non-linear function comprises a square of said amount of non-neutral surface area.

6. A method of predicting binding affinity between first molecule and a second molecule, said method comprising:
    determining a van der Waals interaction energy (vdW) between the first molecule and the second molecule;
    determining a surface contact area of the first molecule forming complimentary polar interactions with the second molecule (Att_pol);
    determining a surface contact area of the first molecule forming uncomplimentary polar interactions with the second molecule (Rep_pol);
    calculating a value of $pK_i$ using at least the determined values of vdW, Att_pol, and Rep_pol.

7. The method of claim 6, wherein calculating a value of $pK_i$ comprises calculating the value of $pK_i$ using a formula $pK_i=C0+C1*vdW+C2*Att\_pol+C3*Att\_pol*Att\_pol+C4*Rep\_pol*Rep\_pol$, wherein C0, C1, C2, C3 and, C4 are constant coefficients.

8. The method of claim 7, wherein C2 is greater than zero, C3 and C1 are less than zero.

9. The method of claim 6, further comprising:
    determining a number of rotatable bonds in the first and second molecules (Rotatable_bond); and
    calculating a value of $pK_i$ using a formula $pK_i=C0+C1*vdW+C2*Att\_pol+C3*Att\_pol*Att\_pol+C4*Rep\_pol*Rep\_pol+C5*Rotatable\_bond$, using the determined values of vdW, Att_pol, Rep_pol, and Rotatable_bond, wherein C0, C1, C2, C3, C4 and C5 are constant coefficients.

10. The method of claim 6, wherein calculating a value of $pK_i$ comprises calculating the value of $pK_i$ using a formula $pK_i=C0+C1*vdW+C2*Att\_pol+C3*(Att\_pol*Att\_pol+Rep\_pol*Rep\_pol)$, based on the determined values of vdW, Att_pol, and Rep_pol, wherein C0, C1, C2 and C3 are constant coefficients.

11. The method of claim 6, wherein determining a van der Waals interaction energy comprises determining the van der Waals energy using a grid-based approximation method.

12. The method of claim 11, wherein determining a van der Waals interaction energy comprises:
    representing the van der Waals interaction energy with one or more original non-linear functions;
    transforming each of the original non-linear functions into a moderated non-linear function, the moderated non-linear function being less non-linear than the original non-linear function;
    for the each of the moderated non-linear functions, applying a trilinear interpolation process to calculate an estimated resulting value of the moderated non-linear function;
    reverse-transforming each of the estimated resulting values of the moderated non-linear functions into an estimated resulting value for each of the original non-linear functions;
    combining the estimated resulting values for each of the original non-linear functions into a combined result; and
    identifying the combined result as the van der Waals interaction energy between the molecule and the protein.

13. A system for predicting binding affinity between a first chemical entity and a second chemical entity, said system comprising:
    a van der Waals energy determination module configured to determine a van der Waals interaction energy between the two chemical entities;
    a complimentary surface area determination module configured to define a surface area of the first chemical entity forming complimentary polar interactions with the second chemical entity;
    an uncomplimentary surface area determination module configured to define a surface area of the first chemical entity forming uncomplimentary polar interactions with the second chemical entity; and
    a calculation module configured to estimate binding affinity between the two chemical entities, using at least the van der Waals energy, the complimentary surface area, and the uncomplimentary surface area.

14. The system of claim 13, wherein the calculation module is configured to calculate a prediction value that represents the predicted binding affinity, the prediction value being at least the sum of a first coefficient, the van der Waals energy multiplied by a second coefficient, the complimentary surface area multiplied by a third coefficient, the square of the complimentary surface area multiplied by a fourth coefficient, and the square of the uncomplimentary surface area multiplied by a fifth coefficient, wherein the first, second, third, fourth and fifth coefficients are constants.

15. The system of claim 14, further comprising a coefficient determination module configured to determine respective values of the first coefficient, the second coefficient, the third coefficient, the fourth coefficient and the fifth coefficient.

16. The system of claim 14, wherein the van der Waals energy determination module is configured to determine a van der Waals energy using a grid-based computation process, wherein the grid-based computation process comprises transforming each of one or more original non-linear functions representing the van der Waals energy into a moderated non-linear function, the moderated non-linear function being less non-linear than the original non-linear function.

17. A method of predicting binding affinity, comprising:

providing a plurality of training items, each of the plurality of training items including a ligand and a protein;

obtaining, for each of the plurality of training items, a van der Waals interaction energy between the ligand and the protein of the training item (vdW);

obtaining, for each of the plurality of training items, a surface area of the ligand forming complimentary polar interactions with the protein (Att_pol);

obtaining, for each of the plurality of training items, a surface area of the ligand forming un-complimentary polar interactions with the protein (Rep_pol);

obtaining, for each of the plurality of training items, a binding affinity between the ligand and the protein ($pK_i$);

determining values of C0, C1, C2 and C3 using a regression technique for the formula $pK_i = C0 + (C1*vdW) + (C2*Att\_pol*Att\_pol) + (C3*(Att\_pol^2 + Rep\_pol^2))$; and estimating an unknown binding affinity using the formula $pK_i = C0 + C1*vdW + C2*Att\_pol + C3*(Att\_pol*Att\_pol + Rep\_pol*Rep\_pol)$ with the determined values of C0, C1, C2 and C3.

18. A method of estimating van der Waals interaction energy comprising:

transforming a function defining said van der Waals energy to a more linear functional form;

computing an estimate of the transformed function defining van der Waals energy using linear interpolation; and transforming the result to correspond to the original linear functional form.

19. The method of claim 18, wherein said computing an estimate comprises linear interpolation.

* * * * *